United States Patent [19]

Schumann

[11] Patent Number: Plant 5,931

[45] Date of Patent: Apr. 7, 1987

[54] GERANIUM PLANT NAMED WALTZ

[75] Inventor: Ingeborg Schumann, Bad Ems, Fed. Rep. of Germany

[73] Assignee: Fischer Geraniums, Inc., Netherlands Antilles

[21] Appl. No.: 761,011

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Waltz having single, large, round flower form and red flower color; green foliage with very strong dark brown leaf zonation; fast rooting; early flowering response and prolific flower production; very good chlorophyll quality for transportation.

1 Drawing Figure

1

The present invention comprises a new and distinct cultivar of geranium, botanically known as *Pelargonium zonale,* and hereinafter referred to by the cultivar name Waltz.

Waltz is a product of a planned breeding program which had the objective of creating new geranium cultivars having black-green zonated foliage with strong leaf zonation, red flower color, single flower form and large flowerhead, very fast rooting, and very good chlorophyll quality for transportation.

Waltz was originated from a hybridization made by Ingeborg Schumann in a controlled breeding program in Hillscheid, Federal Republic of Germany and Galdar, Canary Islands, Spain in 1978. The female parent was a cross between Hönnefrühling and Sincerity. The male parent of Waltz was Bern of the "Pelfi" ® series of Pelargonien-Fischer KG, Hillscheid, Federal Republic of Germany. Both parents are unpatented.

Waltz was discovered and selected as one flowering plant within the progeny of the stated cross by Ingeborg Schumann in July of 1979 in a controlled environment in Galdar, Canary Islands, Spain.

The first act of asexual reproduction of Waltz was accomplished when vegetative cuttings were taken from the initial selection in January of 1980 in a controlled environment in Hillscheid, Federal Republic of Germany by a technician working under formulations established and supervised by Ingeborg Schumann. Horticultural examination of selected units initiated in the spring of 1980 and continued in 1981 through 1983 has demonstrated that the combination of characteristics as herein disclosed for Waltz are firmly fixed and are retained through successive generations of asexual reproduction.

Waltz has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Waltz, which in combination distinguish this geranium as a new and distinct cultivar.

1. Single, large, round flower form, with the umbels being carried on strong, dark reddish peduncles.

2

2. Intense orange-red flower color.
3. Very strong leaf zonation, with the dark green dominant color and zonation contrasting pleasantly with the flower color.
4. Very fast rooting and vigorous growth.
5. Very good chlorophyll quality for transportation.
6. Early flowering, and prolific flower production.

The accompanying photographic drawing shows typical flower and foliage characteristics of Waltz, with colors being as true as possible with illustrations of this type.

In the following description color references are made to The Royal Horticultural Society Colour Chart. The color values were determined between 10:00 a.m. and 11:00 a.m. on May 22, 1985 under 35,000 Lux light intensity at Hillscheid, Federal Republic of Germany.

Classification:

*Botanical.*—A hybrid of the genus *Pelargonium l'hert* and species *Pelargonium zonale.*

*Commercial.*—Waltz.

INFLORESCENCE

A. Umbel:
- *Average diameter.*—129 mm.
- *Average depth.*—72 mm.
- *Peduncle length.*—220 mm.
- *Pedicel length.*—35 mm.

B. Corolla:
- *Average diameter.*—48 mm.
- *Form.*—Single flower; round.
- *Color (general tonality from a distance of three meters).*—Orange-red. Upper surface: 44B.

C. Bud:
- *Shape.*—Elongaged; pointed.
- *Color.*—Orange-red.

D. Reproductive organs:
- *Androecium.*—7–8 stamens.
- *Gynoecium.*—5 lobed stigma.

E. Spring flowering response period: In Hillscheid, Federal Republic of Germany, in 1981, 60% of plants opened with at least one flower 13 weeks after planting of unrooted cuttings.

F. Outdoor flower production: The total flower count in 1981 in Hillscheid, Federal Republic of Germany, was between 55 and 58 flowers per plant for the June through October observation period.

G. Durability: Very good.

PLANT

A. Foliage:

*Form.*—Kidney shaped.

*Margin.*—Generally round, crenate.

*Color.*—Top surface: Main color dark green, generally 137A. Zonation: Very dark brown.

*Tolerance of botrytis.*—Very good.

B. General appearance and form:

*Internode length.*—24 mm.

*Branching pattern.*—3.1 branches per plant.

*Height.*—240 mm.

I claim:

1. A new and distinct cultivar of geranium named Waltz, as described and illustrated, and particularly characterized by its single, large, round flower form and red flower color; green foliage with very strong dark brown leaf zonation; fast rooting; early flowering response and prolific flower production; and very good chlorophyll quality for transportation.

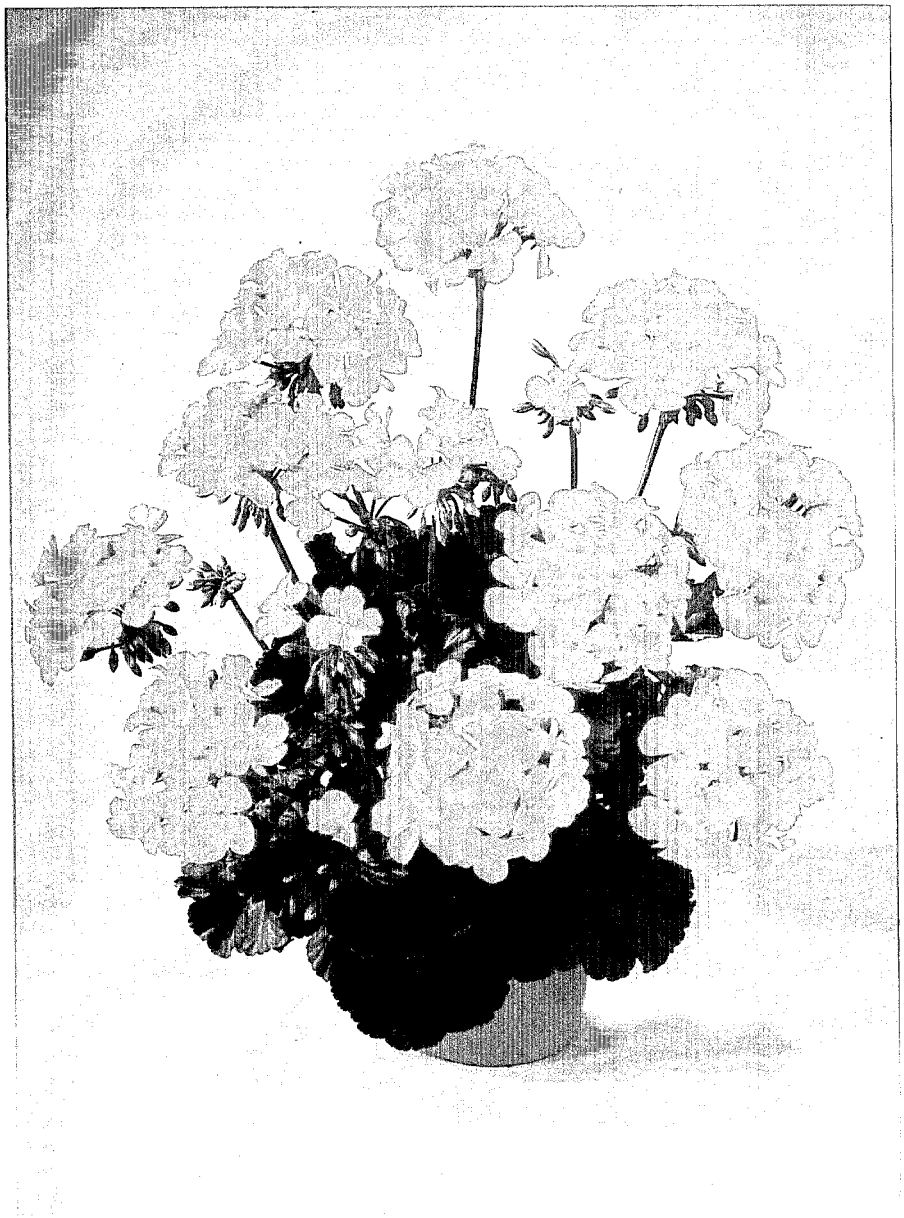

* * * * *